US008864756B2

(12) United States Patent
Strauss

(10) Patent No.: US 8,864,756 B2
(45) Date of Patent: Oct. 21, 2014

(54) HF-SURGERY DEVICE AND METHOD FOR AN HF-SURGERY DEVICE

(75) Inventor: Timo Strauss, Berlin (DE)

(73) Assignee: Celon AG Medical Instruments (DE)

( * ) Notice: Subject to any disclaimer, the term of this patent is extended or adjusted under 35 U.S.C. 154(b) by 599 days.

(21) Appl. No.: 12/681,900

(22) PCT Filed: May 14, 2008

(86) PCT No.: PCT/EP2008/055911
§ 371 (c)(1),
(2), (4) Date: Apr. 7, 2010

(87) PCT Pub. No.: WO2009/053117
PCT Pub. Date: Apr. 30, 2009

(65) Prior Publication Data
US 2010/0217259 A1      Aug. 26, 2010

(30) Foreign Application Priority Data

Oct. 24, 2007   (DE) .................. 10 2007 051 097

(51) Int. Cl.
| A61B 18/18 | (2006.01) |
| A61B 18/12 | (2006.01) |
| A61B 18/00 | (2006.01) |
| A61B 18/14 | (2006.01) |
| A61B 18/16 | (2006.01) |

(52) U.S. Cl.
CPC ... *A61B 18/1233* (2013.01); *A61B 2018/00607* (2013.01); *A61B 2018/00702* (2013.01); *A61B 2018/00875* (2013.01); *A61B 2018/00642* (2013.01); *A61B 18/1477* (2013.01); *A61B 18/16* (2013.01)
USPC ......................................................... 606/35

(58) Field of Classification Search
USPC ................................................... 606/35, 34
See application file for complete search history.

(56) References Cited

U.S. PATENT DOCUMENTS 3,933,157 A    1/1976   Bjurwill et al. .......... 128/303.14
4,416,276 A *  11/1983  Newton et al. ................. 606/35
(Continued)

FOREIGN PATENT DOCUMENTS

| DE | 28 01 833 | 1/1978 |
| DE | 35 44 443 | 6/1987 |

(Continued)

OTHER PUBLICATIONS

International Search Report mailed Oct. 27, 2008 in corresponding PCT International No. PCT/EP2008/055911.

(Continued)

*Primary Examiner* — Michael Peffley
*Assistant Examiner* — Daniel Fowler
(74) *Attorney, Agent, or Firm* — Ostrolenk Faber LLP

(57) ABSTRACT

The invention concerns an HF-surgery device for cutting and/or coagulating biological tissue and a method for same, which in operation monitors the patient skin contact of a connected neutral electrode having at least two separate contact surfaces. The HF-surgery device includes at least one parallel resonant circuit arranged in a patient circuit, at least one measurement energy source arranged in a measurement circuit galvanically separated from the patient circuit for producing a measurement voltage/current acting between the contact surfaces of the neutral electrode, and at least one measuring and computing unit which in operation determines by means of the measurement voltage/current a tissue impedance which is representative of the patient skin contact and which acts between the contact surfaces. An HF-current flows in the patient circuit which is closed in the cutting or coagulation operation and the measurement voltage which is independent of the HF-current can be produced in the measurement circuit. To provide an improved HF-surgery device it is provided according to the invention that the frequency of the measurement voltage source is substantially equal to a resonance frequency of the parallel resonant circuit.

9 Claims, 1 Drawing Sheet

(56) References Cited

U.S. PATENT DOCUMENTS

| | | | |
|---|---|---|---|
| 4,494,541 A * | 1/1985 | Archibald | 606/35 |
| 4,754,757 A | 7/1988 | Feucht | |
| 5,087,257 A * | 2/1992 | Farin et al. | 606/35 |
| 5,372,596 A * | 12/1994 | Klicek et al. | 606/35 |
| 5,971,981 A * | 10/1999 | Hill et al. | 606/35 |
| 6,860,881 B2 * | 3/2005 | Sturm et al. | 606/35 |
| 7,160,293 B2 | 1/2007 | Sturm et al. | 606/35 |
| 2004/0059323 A1 | 3/2004 | Sturm | |
| 2007/0073284 A1 | 3/2007 | Sturm et al. | 606/35 |
| 2007/0222458 A1 * | 9/2007 | Eisele | 324/633 |

FOREIGN PATENT DOCUMENTS

| | | |
|---|---|---|
| DE | 41 26 607 | 2/1993 |
| DE | 197 14 972 | 10/1998 |
| DE | 10 2004 025 613 | 12/2005 |
| EP | 0 390 937 | 10/1990 |
| JP | 62-155841 | 7/1987 |
| JP | 2003-080846 | 3/2003 |
| JP | 2006-500165 | 1/2006 |
| JP | 2008-500080 | 1/2008 |
| WO | WO 93/03677 | 3/1993 |
| WO | WO 03/090634 | 11/2003 |
| WO | WO 2005-115262 | 12/2005 |

OTHER PUBLICATIONS

Office Action issued by German Patent Office in connection with corresponding application No. 2010-530365 on Dec. 21, 2012.
Search Report issued by European Patent Office on Apr. 23, 2014 in connection with corresponding EP patent application No. EP 12 16 9662.

* cited by examiner

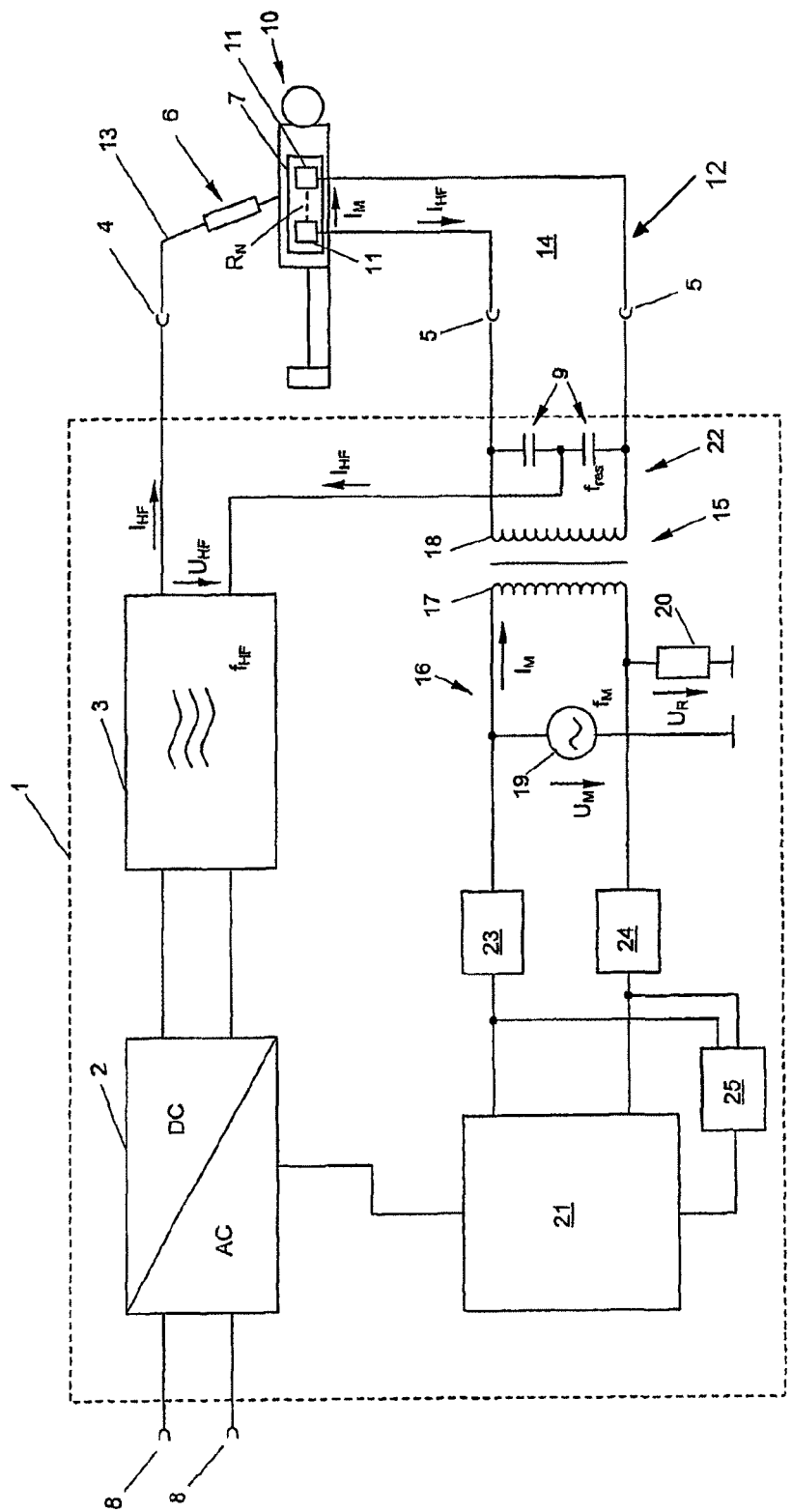

HF-SURGERY DEVICE AND METHOD FOR AN HF-SURGERY DEVICE

CROSS-REFERENCE TO RELATED APPLICATIONS

The present application is a 35 U.S.C. §§371 national phase conversion of PCT/EP2008/055911, filed May 14, 2008, which claims priority of German Patent Application No. 10 2007 051 097.9, filed Oct. 24, 2007. The PCT International Application was published in the English language.

BACKGROUND OF THE INVENTION

The invention concerns an HF-surgery device for cutting and/or coagulating biological tissue, which in operation monitors the patient skin contact of a connected neutral electrode having at least two separate contact surfaces. The HF-surgery device includes at least one parallel resonant circuit arranged in a patient circuit, at least one measurement energy source arranged in a measurement circuit galvanically separated from the patient circuit for producing a measurement voltage/current acting between the contact surfaces of the neutral electrode, and at least one measuring and computing unit which in operation determines by means of the measurement voltage/current a tissue impedance which is representative of the patient skin contact and which acts between the contact surfaces. An HF-current flows in the patient circuit which is closed in the cutting or coagulation operation and the measurement voltage which is independent of the HF-current can be produced in the measurement circuit.

The invention further concerns a method for an HF-surgery device for monitoring the skin contact of a neutral electrode which is electrically connected to the HF-surgery device and which has at least two separate contact surfaces. In the method a measurement voltage/current is produced in a measurement circuit, the measurement voltage/current is transferred from the measurement circuit into a galvanically separated patient circuit in which an HF-current flows in operation in the closed condition, the measurement voltage/current in the patient circuit is passed by way of a parallel resonant circuit and the tissue between the contact surfaces and the tissue impedance representative of the patient skin contact is determined by means of the measurement voltage/current.

HF-surgery devices and methods of the above-indicated kind are known from the state of the art. The high frequency (HF)-surgery devices are used for cutting and/or coagulating biological tissue. An active electrode is usually connected to the HF-surgery device. An active electrode has a small current transmission surface in order to achieve a high level of current density. The active electrode is guided by the physician in the treatment and passes the HF-current into the body of the patient. In addition, one or more neutral electrodes connected to the patient are connected to the HF-surgery device for the return flow of the current.

Neutral electrodes are electrodes of relatively large surface area for application to the body of a patient. They serve to form a return flow path for the high frequency current at such a low current density in the body tissue that unwanted physical effects such as burns are avoided. The neutral electrode was intended to be reliably applied with its entire surface area against the body of the patient. In addition care is to be taken to ensure that secure contact of the neutral electrode is ensured for the entire duration of the high frequency use.

Divided neutral electrodes have at least two contact surfaces which are electrically insulated from each other and which are applied to the skin of the patient in mutually juxtaposed relationship and make electrical contact with the skin. Fitted to the patient, the tissue between the contact surfaces represents an electrical connection whose resistance changes with the size of the connecting area. Instead of a divided neutral electrode with separate contact surfaces it will be appreciated that it is also possible to use two or more neutral electrodes.

Various devices are known which are intended to automatically monitor the skin contact of the neutral electrode and, in the event of inadequate contacting with the body of the patient, generate warning signals and/or switch off the high frequency application.

It is known for an auxiliary or measurement current to be passed by way of the contact surfaces of the divided neutral electrode and monitored. The measurement circuit into which the measurement current is fed is galvanically separated from the patient circuit in which the HF-current flows by way of the active and neutral electrodes during use. The skin contact of the neutral electrode can be monitored by the tissue impedance between the two electrode portions being ascertained and observed. A measuring and computing unit of the HF-surgery device can implement continuous checking of the neutral electrode and deliver suitable warning or switch-off signals.

Methods and apparatuses for contact monitoring of neutral electrodes are known for example from DE 32 49 766, DE 35 44 443 or EP 0 390 937.

DE 197 14 972 discloses an apparatus for contact monitoring of a neutral electrode comprising a resonant circuit that is activated by alternating voltage of varying frequencies and arrange of a resonant frequency and that provides a peak reading detector, which records a peak reading of the alternating voltage occurring in the resonance frequency.

U.S. Pat. No. 7,160,293 discloses a multiple radio-frequency return pad contact detection system that eliminates or minimizes interference or measurement interaction between a plurality of pad pairs by providing a different signal source frequency for each pad contact pair, but a frequency which matches an associated series resonant network frequency.

DE 10 2004 025 613 discloses an apparatus that determines a transient impedance between two parts of a two part neutral electrode.

The known methods and circuit arrangements suffer from the disadvantage that the quality of skin contact monitoring can fluctuate. In particular it has been found that, from impedances of higher than about 130 ohms, which can be caused for example by an increased proportion of fat in the tissue, detectability of an inadequately arranged neutral electrode deteriorates.

SUMMARY OF THE INVENTION

Therefore the object of the present invention is to provide an HF-surgery device and a method for an HF-surgery device, which reliably monitors the skin contact of a connected neutral electrode even when high tissue impedances are involved.

In the HF-surgery device according to the invention that object is attained in that the frequency of the measurement voltage source is substantially equal to a resonance frequency of the parallel resonant circuit.

The method according to the invention attains that object in that the frequency of the measurement voltage/current is set substantially to a resonance frequency of the parallel resonant circuit.

The invention has the advantage that the influence of the components in the parallel resonant circuit on the measurement current or the measurement voltage is minimised. The resistance of the parallel resonant circuit becomes at a maximum at its resonance frequency. In operation, when the neutral electrode is connected to the HF-surgery device, the transition or tissue resistance between the contact surfaces of the neutral electrode and the parallel resonant circuit form a parallel circuit. In a parallel circuit, the reciprocal value of the total resistance is formed by the sum of the reciprocal values of the individual resistances. At maximum resistance of the parallel resonant circuit therefore the influence of the components of the parallel resonant circuit on the measurement current tends towards zero or is negligibly low. It has been found that skin contact of the neutral electrode can be accurately detected by means of the invention even with tissue impedances of greater than 130 ohms.

The invention can be further developed by various advantageous configurations. Such configurations are described hereinafter.

Thus the HF-surgery device can have a transformer galvanically separating the measurement circuit from the patient circuit. At the same time the parallel resonant circuit can include a secondary side of the transformer, that is associated with the patient circuit, and at least one anti-faradisation capacitor. More specifically anti-faradisation capacitors are provided for avoiding direct currents in the patient current, which are dangerous to the patient. This advantageous embodiment has the advantage that an influence of the anti-faradisation capacitors, which causes disturbance in terms of measuring procedure, is minimised, and at the same time this affords a simple structure with few individual components.

According to the invention the tissue impedance can be determined at the transformer which separates the measurement circuit from the patient circuit. In order to be able to easily calculate that impedance at the transformer side arranged in the measurement circuit, the HF-surgery device can have in the measurement circuit at least one measurement resistor connected in series with the transformer. The measuring and computing device which is connected to the measurement circuit in regard to the signal aspect measures for example the voltage across the voltage source and the voltage at the measurement resistor. The impedance at the transformer representing the tissue impedance can be easily calculated from the two voltage values and the known resistance of the measurement resistor.

In addition the HF-surgery device can include a phase angle measurement unit which measures a phase shift angle between the measurement current and the measurement voltage or between proportional values of the measurement current and the measurement voltage. At the same time the measuring and computing unit can be adapted to determine the effective tissue resistance representative of the patient skin contact between the contact surfaces by means of the phase shift angle. Thus the effective tissue resistance which is more informative can be calculated from the tissue impedance of the neutral electrode. The impedance comprises the real effective resistance and the imaginary reactive impedance. The reactive impedance is not significant regarding the risk of burning at the neutral electrode, but is increased for example due to the capacitive action of the neutral electrode bearing against the skin. Therefore the tissue impedance is falsified by the reactive resistance, in relation to the patient skin contact to be determined. Values proportional to the measurement current and the measurement voltage are for example the voltage drop across the measurement current source and the voltage drop across a measurement resistor. That is advantageous because voltage measurement is easier to implement than current measurement.

In order to eliminate disturbances in the measurement current or the measurement voltage due to the HF-current of the patient circuit, the HF-surgery device can have at least one filter unit for filtering the measurement current and/or the measurement voltage. The filter unit is preferably arranged in the measurement circuit, upstream of the measurement and computing unit in relation to the signals involved. The filter unit limits the measurement signal to frequencies around the measurement current frequency, that is to say the resonance frequency of the parallel resonant circuit. The filter unit thus acts in addition to the parallel resonant circuit which also already has a filtering action in the region of the resonance frequency.

BRIEF DESCRIPTION OF THE DRAWINGS

The invention is described hereinafter with reference to the accompanying drawings by way of example. The different features can be combined as desired, like the above-described configurations.

In the drawings:

FIG. 1 shows a simplified schematic block circuit diagram of an HF-surgery device according to the invention with connected active and neutral electrodes.

DETAILED DESCRIPTION OF THE INVENTION

An HF-surgery device 1 for cutting and/or coagulating biological tissue has a mains unit 2, a frequency generator 3 and connecting contacts 4, 5 for an active electrode 6 and a neutral electrode 7.

The mains unit 2 can be connected to a mains voltage source (not shown) by way of mains contacts 8. The frequency generator 3 is coupled at its input side to the mains unit 2. At the output side the frequency generator 3 is connected on the one hand to the connecting contact 4 for the active electrode 6 and on the other hand to the connecting contacts 5 for the neutral electrode 7. A respective anti-faradisation capacitor 9 is arranged between the frequency generator 3 and the two connecting contacts 5 for the divided neutral electrode 7.

As shown in FIG. 1, connected to the connecting contact 4 is an active electrode 6, for example a cutting or coagulation electrode. The neutral electrode 7 is applied to the skin of the patient 10 in known manner. The neutral electrode 7 is in the form of a divided neutral electrode 7 and has two contact surfaces 11 which are electrically separated from each other and which are each in electrical contact with the skin of the patient. The contact surfaces 11 are therefore connected together only by way of the electrically conductive tissue of the patient 10.

In operation of the HF-surgery device 1 the alternating current which is fed in by way of the mains contacts 8 is converted into a direct current which then flows to the frequency generator 3. The direct current is converted by the frequency generator 3 into a high-frequency alternating current $I_{HF}$ which is usual for high-frequency surgery, at a frequency $f_{HF}$ of about 300 to 450 kHz.

The frequency generator 3 is part of a patient circuit 12 in which the HF-current $I_{HF}$ flows in an active path 13 from the frequency generator 3 to the active electrode 6. The active path 13 is the part, disposed upstream of the patient 10 in FIG. 1, of the patient circuit 12 which extends from the frequency generator 3 to the active electrode 6. Upstream of the active electrode 6 the HF-current $I_{HF}$ flows by way of the patient 10 to the contact surfaces 11 of the neutral electrode 7. When passing into or passing from the active electrode 6 to the biological tissue of the patient 10 the HF-current produces the desired surgical effect such as cutting and/or coagulation.

A passive path 14 of the patient circuit 12 extends from the neutral electrode 7 to the frequency generator 3 and is downstream of the patient in FIG. 1. In operation the HF-current $I_{HF}$ flows in the passive path 14 from the contact surfaces 11 of the neutral electrode 7 back to the frequency generator 3 by way of one of the two anti-faradisation capacitors 9. The anti-faradisation capacitors 9 minimise direct currents and currents of low frequency, which are dangerous to the patient, and are for example of a size of about 50 to 100 nF.

Defective or inadequate application and thus inadequate electrical contact of the neutral electrode 7 against the patient 10 can lead to burns at the contact surfaces. A transition resistance or tissue resistance $R_N$ between the contact surfaces 11 of the neutral electrode 7 is representative of the contact between the neutral electrode 7 and the skin of the patient.

For determining the tissue resistance $R_N$, a measurement voltage $U_M$ or a measurement current $I_M$, acting between the contact surfaces 11, is fed into the passive path 14 of the patient circuit 12. The smaller the contact between the contact surfaces 11 and the skin, the lower the tissue resistance $R_N$ also is. In that respect the measurement current $I_M$ flows from the one contact surface 11 by way of the tissue of the patient 10 to the other contact surface 11.

A measurement voltage source 19 for generating the measurement current $I_M$ is arranged in a measurement circuit 16. In order to galvanically separate the measurement circuit 16 from the patient circuit 12, a transformer 15 is provided in the HF-surgery device 1. Thus, the measurement voltage source 19 is arranged at an intermediate circuit level which is decoupled from the patient. The transformer 15 has a primary side 17 arranged in the measurement circuit 16 and a secondary side 18 arranged in the patient circuit 12. In the embodiment in FIG. 1 the number of turns on the primary and secondary sides 17, 18 is the same. In addition, a series-connected measurement resistor 20 is provided in the measurement circuit 16, beside the transformer 15 and the measurement voltage source 19.

The inductance of the secondary side 18 of the transformer 15 forms a parallel resonant circuit 22 together with the capacitance of the two anti-faradisation capacitors 9 which are connected in parallel. In that case the anti-faradisation capacitors 9 are arranged in parallel with the tissue resistance $R_N$ of the neutral electrode 7.

The HF-surgery device 1 also has a measuring and computing unit 21 which is connected to the measurement circuit 16 in respect of the signals involved. In the case of the HF-surgery device in FIG. 1 the measuring and computing unit 21 takes off signals at two locations, between the measurement energy source 19 and the primary side 17 as well as between the primary side 17 and the measurement resistor 20. The measuring and computing unit 21 is additionally coupled in respect of the signals involved to the mains unit 2. Two band pass filters 23, 24 are disposed between the measuring and computing unit 21 and the measurement circuit 16. A phase angle measurement unit 25 for measuring the phase shift angle between the above-mentioned signals is also connected in respect of the signals involved to the measuring and computing unit 21.

In operation of the HF-surgery device 1 the measurement voltage source 19 produces the measurement current $I_M$ at a measurement frequency $F_M$, independently of the HF-current in the patient circuit 12. The measurement frequency $f_M$ of the measurement voltage source 19 is so set that it is substantially equal to a resonance frequency $f_{res}$ of the parallel resonant circuit 22.

The resonance frequency $f_{res}$ in the parallel resonant circuit 22 is determined by the magnitudes of its inductance and capacitance. As is known the following applies:

$$f_{res} = \frac{1}{2\pi\sqrt{LC}},$$

wherein L is the magnitude of the inductance and C that of the capacitance.

In the HF-surgery device 1 shown by way of example in FIG. 1 the measurement frequency $f_M$ and the resonance frequency $f_{res}$ are for example about 75 kHz. In the ideal case, in the steady-state condition, the impedance of the parallel resonant circuit 22 is infinitely large at the resonance frequency $f_{res}$. In practice the impedance is at least negligibly large. The parallel resonant circuit 22 is connected in parallel with the tissue resistance $R_N$ of the neutral electrode 7. As the reciprocal value of the total impedance of a parallel circuit is determined by the sum of the reciprocal values of the individual impedances, the reciprocal value of the impedance of the parallel resonant circuit 22 becomes very low and as a result is of no significance. Consequently the joint impedance of the tissue resistor $R_N$, the parallel resonant circuit 22 and the lines therebetween is substantially equal to the tissue resistance $R_N$.

The action of the transformer 15 provides that that joint impedance is transferred from the secondary side 18 to the primary side 17. It follows therefrom that the complex resistance—the impedance—at the primary side 17 of the transformer 15 substantially corresponds to the tissue resistance $R_N$ representative of the skin contact. The impedance at the primary side 17 can be determined as described hereinafter.

To determine the impedance at the primary side 17 of the transformer 15 the measuring and computing unit 21 measures both the voltage drop $U_M$ at the measurement voltage source 19 and also the voltage drop $U_R$ at the measurement resistor 20. For that purpose the measuring and computing unit 21 takes off the voltage $U_M$ between the voltage source 19 and the primary side 17. A second voltage $U_R$ is taken off between the primary side 17 and the measurement resistor 20.

As the measurement current $I_M$ oscillates with the resonance frequency $f_{res}$ of the parallel resonant circuit 22 the parallel resonant circuit 22 has an advantageous filtering action on the measurement current and measurement voltage. In order to avoid permanent disturbances in the measurement current and the measurement voltage due to the HF-current $I_{HF}$ the signals which are taken off by the measuring and computing unit 21 are additionally filtered. The two band pass filters 23, 24 are provided for that purpose.

The measuring and computing unit 21 can calculate the impedance at the primary side 17, that corresponds to the tissue impedance, from the measured voltages $U_M$ and $U_R$.

As is known, impedance, that is to say apparent resistance, is composed of the reactance and effective resistance. The risk of burning to the patient at the neutral electrode 7 is represented in particular by the effective resistance and less by the reactance. The reactance in contrast is increased by the capacitive action of the contact surfaces 11 of the neutral electrode 7 on the skin of the patient 10. An advantage of the HF-surgery device 1 shown in FIG. 1 lies in evaluation of the effective tissue resistance which more reliably reflects the skin contact than only the tissue impedance.

The HF-surgery device shown in FIG. 1 and in particular the measuring and computing unit 21 calculates the effective resistance by means of the phase shift angle between the voltages $U_M$ and $U_R$ measured in the measurement circuit 16. The phase shift angle is determined by the phase angle measurement unit 25 and passed to the measuring and computing unit 21. The phase angle measurement unit 25 is connected in respect of the signals involved to the output of the two band pass filters 23, 24 to take off the filtered voltages $U_M$ and $U_R$.

If the tissue impedance or effective tissue resistance ascertained by the measuring and computing unit 21 exceeds a predetermined limit value the measuring and computing unit 21 can send a switching signal to the mains unit 2. The switching signal can switch off the mains unit 2 and/or the frequency generator 3 or reduce the power output thereof. Thus no or only very little HF-current can flow in the patient circuit 12 and possible burns at the neutral electrode 7 are prevented. Additionally or alternatively the ascertained tissue impedance representative of patient skin contact, or effective resistance, can trigger an operational and/or warning signal, depending on whether the value in question exceeds or falls below the limit value. The operational and warning signal can be for example signal lamps or acoustic signals actuated by the measuring and computing unit 21.

The invention claimed is:

1. An HF-surgery device configured for at least one of cutting and coagulating of biological tissue,
   the device is configured to monitor a skin contact to a patient, of a connected neutral electrode having at least two separate contact surfaces, the device including at least one parallel resonant circuit arranged in a patient circuit,
   wherein at least one measurement energy source is arranged, in a measurement circuit galvanically separated from the patient circuit, and configured for producing at least one of a measurement voltage or current acting between the contact surfaces of the neutral electrode, and
   the device including at least one measuring and computing unit which is configured to determine, by means of the at least one of measurement voltage or current, as applicable, a tissue impedance, which is representative of the patient skin contact, between the contact surfaces,
   wherein an HF-current flows in an electrically closed patient circuit, during the cutting or coagulation operation, and whereby the measurement voltage, which is independent of the HF-current, can be produced in the measurement circuit,
   wherein the frequency of the measurement voltage source is substantially equal to a resonance frequency of the parallel resonant circuit and, wherein the HF-surgery device includes a phase angle measurement unit which measures a phase shift angle between the measurement current and the measurement voltage or between values proportional to the measurement current and the measurement voltage, and
   the measuring and calculating unit is adapted to determine the effective resistance representative of the patient skin contact between the contact surfaces by means of the phase shift angle.

2. An HF-surgery device according to claim 1, wherein the HF-surgery device has at least one filter unit for filtering at least one of the measurement current and the measurement voltage.

3. An HF-surgery device according to claim 1, wherein the HF-surgery device has in the measurement circuit at least one measurement resistor connected in series with the transformer.

4. An HF-surgery device according to claim 1, wherein the HF-surgery device has a transformer galvanically separating the measurement circuit from the patient circuit and the parallel resonant circuit includes a secondary side of the transformer, that is associated with the patient circuit, and at least one anti-faradisation capacitor.

5. An HF-surgery device according to claim 4, wherein the HF-surgery device has in the measurement circuit at least one measurement resistor connected in series with the transformer.

6. A method for monitoring the skin contact of a neutral electrode which is electrically connected to an HF-surgery device having at least two separate contact surfaces, in which a measurement voltage/current is produced in a measurement circuit, comprising the steps of:
   transferring the measurement voltage/current from the measurement circuit into a galvanically separated patient circuit in which an HF-current flows in operation in an electrically closed condition of the patient circuit,
   providing the measurement voltage/current in the patient circuit by way of a parallel resonant circuit, and
   determining impedance of the tissue between the contact surfaces with the tissue impedance being representative of the patient skin contact by means of the measurement voltage/current,
   setting the frequency of the measurement voltage/current substantially to a resonance frequency of the parallel resonant circuit,
   determining a phase shift angle between the measurement current and the measurement voltage or between proportional values to the measurement current and the measurement voltage, and
   determining an effective resistance of the tissue between the contact surfaces, representative of the patient skin contact of the neutral electrode, from the impedance and the phase shift angle.

7. A method according to claim 6, wherein a voltage across a measurement energy source and a voltage across a series-connected measurement resistor are measured to determine the tissue impedance in the measurement circuit.

8. A method according to claim 7, wherein at least one of the voltage across the measurement energy source and the voltage across the series connected measurement resistor is filtered prior to the measurement operation.

9. A method according to claim 6, wherein, in dependence on the value of the effective resistance, at least one of a warning signal is delivered and the patient circuit of the HF-surgery device is interrupted.

* * * * *